United States Patent [19]
Spielvogel

[11] Patent Number: 5,256,394
[45] Date of Patent: Oct. 26, 1993

[54] RADIOLOGICAL IMAGING METHOD, AND CONTRAST MEDIA REAGENTS THEREFOR

[75] Inventor: Bernard F. Spielvogel, Raleigh, N.C.

[73] Assignee: Boron Biologicals, Inc., Raleigh, N.C.

[21] Appl. No.: 781,812

[22] Filed: Oct. 23, 1991

[51] Int. Cl.$^5$ .............................................. A61K 49/04
[52] U.S. Cl. ........................................ 424/5; 423/275;
423/284; 423/289; 423/290; 423/291; 423/292;
423/293; 424/4; 424/450; 514/64; 530/300;
530/332; 530/350; 530/395; 530/397; 536/1.11;
536/7.3; 536/17.1; 536/22.1
[58] Field of Search .................... 564/8, 9, 13, 10, 11;
424/4, 5; 423/276, 284, 300, 302; 568/2, 3, 4, 5;
514/114, 118

[56] References Cited

U.S. PATENT DOCUMENTS

| | | | |
|---|---|---|---|
| 3,314,990 | 4/1967 | Miller et al. | 260/551 |
| 4,412,053 | 10/1983 | Neilson et al. | 528/30 |
| 4,451,400 | 5/1984 | Wiezer | 544/113 |
| 4,523,009 | 6/1985 | Neilson et al. | 528/399 |
| 4,971,897 | 11/1990 | Chen et al. | 564/13 |

OTHER PUBLICATIONS

Biodegradable Polymers Are Drug Delivery Systems, Langer, R. & Chasin, M. "Polyphosphazenes as New Biomedically and Bioactive Materials" pp. 163-193 (1990).
Cohen, S., et al "Ionically Cross-Linkable Polyphosphazene: A Novel Polymer for Microencapsulization", J. Am. Chem. Soc. (1990) 7832-7833.
Spielvogel, B. E., et al, "Polyphosphazenes/The Emergence of Inorganic Polymers" Army Research, Deve. & Acquisition Magazine, (Sep.-Oct. 1985), pp. 21-22.
Langer, R. "New Methods of Drug Delivery", Science, vol. 249, pp. 1527-1533, (Sep. 28, 1990).
Facchin et al., *J. Inorg. Organomet. Polym.*, 1(3) pp. 389-395 (1991) (Chem. Abs. 116:255791q).
Volodin et al. *Chem. Abs.*, 77:114370r (1972).
Kireev et al., *Chem. Abs.*, 83: 96172v (1975).
Telkova et al., *Chem. Abs.*, 79: 115244f (1973).
Harris et al., *Chem. Abs.*, 100: 6639v (1984).
Harris, *Inorg. Chim. Acta*, 71, pp. 233-237 (1983).
Allcock et al., *Inorg. Chem.*, 19(4), pp. 1026-1030 (1980).
Allcock et al., *Inorg. Chem.*, 20(9), pp. 2844-2848 (1981).
Allcock et al., *Organometallics*, 2(11), pp. 1514-1523 (1983).

*Primary Examiner*—Allen J. Robinson
*Assistant Examiner*—Scott C. Rand
*Attorney, Agent, or Firm*—Steven J. Hultquist

[57] ABSTRACT

A method of imaging a corporeal situs by radiological techniques, comprising delivery to the corporeal situs of an imagingly effectively amount of a physiologically acceptable composition comprising a boron reagent. A variety of illustrative boron reagents is described, including iodinated boron salts, and boron-containing cyclophosphazene and polyphosphazene reagents having radiopaque character. The reagents and method of the present invention may be employed for a wide variety of radiological imaging applications, e.g., excretory urography, angiocardiography, and aortography.

7 Claims, No Drawings

RADIOLOGICAL IMAGING METHOD, AND CONTRAST MEDIA REAGENTS THEREFOR

BACKGROUND OF THE INVENTION

1. Field of the Invention

This invention relates to a method of imaging a visualizable corporeal situs by radiological imaging techniques, comprising delivery of the situs of an imagingly effective amount of an imagingly effective, physiologically acceptable reagent, as well as to contrast media reagents useful for such imaging.

2 Description of the Related Art

In fields such as angiography and gynecology, as well as in other medical diagnostic and treatment fields, radiological imaging reagents are employed. These reagents are typically delivered to the corporeal situs to be visualized, and then the associated corporeal region is subjected to radiation (e.g., X-ray) exposure and fluoroscopic analysis.

By way of example, radiological reagents (sometimes hereinafter referred to as "contrast media", "contrast media reagents", or "imaging reagents") are delivered to a coronary situs in coronary angioplasty by means of an angiographic syringe or injector, which directs the contrast media through a catheter or other passage means into the appropriate coronary lumen. Vascular plaques are similarly visualized by catheter-mediated introduction of contrast medium to the vascular lumen, in connection with potential use of arterial angioplasty techniques (e.g., balloon angioplasty or laser angioplasty), by means of which the vascular plaque is treated to deocclude the arterial lumen. In gynecological diagnosis, an imaging reagent may be transcervically introduced by a syringe, pump, or injector, following which the pelvic region is radiologically visualized.

Contrast media reagents comprise a constituent imparting radiopacity thereto, typically an iodine-based compound which is physiologically acceptable, e.g., organically-bound iodine, or iron chelate complexes of iodine. Examples of commercially available iodine-based radiological imaging reagents include the iodine-based radiopaque contrast medium formulation which is commercially available under the trademark VASCORAY ® from Mallinckrodt Corporation (St. Louis, Mo.).

Among the deficiencies attending the use of conventional iodine-based radiological imaging formulations is the fact that the active ingredients imparting radiopacity to the contrast medium formulation typically are not degradable into physiologically acceptable by-products and residues. Accordingly, the contrast medium must be completely removed (flushed, or otherwise extracted) from the corporeal system following visualization of the desired situs.

Second, the active ingredient of such conventional imaging formulations frequently has a relatively low concentration or "loading" of iodine associated therewith, as a result of which relatively high dosages of the contrast medium are required.

Third, the active ingredients employed in radiological imaging formulations frequently are poorly soluble in the carrier medium of the formulation.

Accordingly, it would be a substantial advance in the art to provide a radiological imaging reagent which (i) is physiologically acceptable, (2) is highly effective, (3) comprises an active ingredient which is water soluble so that water may be employed as the solvent medium of the reagent formulation, (4) is degradable to physiological acceptable by-products and residues, which are readily metabolized and/or excreted in normal functioning of the corporeal system, and (5) is characterized by a high concentration or loading of iodine.

Relative to the radiological visualizing method, and contrast media reagent species of the present invention, relevant art is described below.

U.S. Pat. No. 4,847,065 to A. Y. Akimova et al discloses iodine-containing radiopaque organic acids, as described at column 3, lines 15–21 of the patent.

U.S. Pat. No. 4,713,235 to R. E. Krall discloses organic iodo agents, particularly iodo carboxylic acids, as radiopaque agents in acrylate-based occlusion compositions for female sterilization. The iodine reagents are discussed at column 3, line 20 to column 4, line 22 of the patent.

As mentioned above, a diagnostic radiopaque formulation is commercially available from Mallinckrodt, Inc. (St. Louis, Mo.) under the trademark VASCORAY ®. This contrast media formulation is a phosphate-buffered solution containing organically bound iodine.

Commercially available diagnostic radiopaque media are variously used in aortography, angiocardiography, and excretory urography.

SUMMARY OF THE INVENTION

In one aspect, the present invention relates to a method of radiologically visualizing a corporeal situs, comprising delivery to the situs of an imagingly effective amount of a physiologically acceptable contrast medium formulations comprising a radiopacity-imparting boron compound, followed by visualizing the coporeal situs with radiological imaging means.

As used herein, the term "physiologically acceptable" means that the contrast medium is biocompatible in character, with respect to its administration, contact, and action in the corporeal system with which the contrast medium is used. The term "imagingly effective" means efficacious for radiological imaging using a radiation source and visualizing means, e.g., X-ray source and fluoroscopic visualizing means.

In a specific aspect, the contrast medium employed in the method broadly described hereinabove, may suitably comprise a halogenated (iodinated) boron compound. As used herein, the term "boron compound" is intended to be broadly construed to include a compound, ionic (anionic, cationic, zwitterionic) moiety, and/or coordinating complex containing at least one boron atom as a constituent thereof.

Correspondingly, a halogenated boron compound is a boron compound having halo atoms as constituents thereof. The halo moiety may suitably comprise fluorine, chlorine, bromine, and/or iodine, and in a preferred aspect, the halogenated boron compound contains iodine.

The preferred iodine-containing boron compounds may suitably comprise iodine-containing borohydride salts, iodine-containing ionic moieties, and/or derivatives of such salts and ionic moieties. Alternatively, the iodine-containing boron compound may suitably comprise a polyphosphazene or other inorganic polymer, as a backbone structure to which iodine-containing moieties are pendently bonded or otherwise associated. Preferably, such polymeric iodine-containing boron compounds comprise functional groups imparting water solubility to the polymer, and most preferably, the polymer comprises functionality which imparts water solubility as well as hydrolytic character, whereby the polymer may be degraded in vivo, e.g., to physiologically acceptable hydrolysis reaction products which are readily bioassimilated by and/or excreted from the corporeal system.

In another aspect, the present invention relates to specific boron compounds having utility in contrast media of the invention, e.g., as an active (radiopacity-imparting) ingredient in a contrast medium formulation. These novel diagnostic imaging compounds include various halogenated (iodinated) boron compounds, and their corresponding derivatives.

Still other aspects of the invention include methods of making various specific imaging compounds, such as halogenated (iodinated) boron compounds, hereinafter more fully described.

DETAILED DESCRIPTION OF THE INVENTION, AND PREFERRED EMBODIMENTS THEREOF

The present invention is based on the surprising and unexpected discovery that useful contrast media reagents may be based on boron compounds, including boron compounds known heretofore e.g., iodine-containing borohydride compounds and derivatives, as well as novel boron compounds including the cyclophosphazene and polyphosphazene boron compounds hereinafter more fully described.

Among the boron compounds which may be usefully employed as contrast media active ingredients in the broad practice of the present invention are the boron compounds illustratively identified below:

1. boron analogs of the carbon-based reagents used in conventional X-ray imaging applications (the conventional reagents typically being benzene derivatives which are iodinated), as well as iodinated carboranes;

2. halogenated (iodinated) salts of borohydrides, particularly iodinated boron salts of the formula:

$$M_a B_x H_y I_z,$$

wherein:

M is an alkali metal or alkaline earth metal;
a is 1 when M is divalent and 2 when M is monovalent;
x is 10 or 12;
y is from 0 to 10; and
z is from 2 to 12,
and derivatives thereof, including ionic, and particularly anionic, species thereof;

3. polyphosphazene boron compounds, including polyphosphazenes of the following formula:

$$A_1 \mathrm{-\!\!\!-\!\!\![N\!\!=\!\!P]_{\mathit{n}}\!\!-\!\!\!-} A_2$$
$$\overset{\displaystyle R_1}{\underset{\displaystyle R_2}{|}}$$

wherein:

$A_1$, and $A_2$ are end groups independently selected from hydrogen, halo, and organo which preferably are of a suitable organic constituency which is compatible with the polyphosphazene and does not preclude its efficacy for radiological imaging purposes - $A_1$ and $A_2$ therefrom may be the same or different, and may for example comprise alkyl or other hydrocarbyl radicals;

$R_1$ and $R_2$ may be the same or different, and are independently selected from hydrogen, halo, and organo groups (e.g., alkyl, haloalkyl, aryl, arylalkyl, alkenyl, alkylamino, arylamino, etc.); and n is from 2 to 20,000;

with the proviso that at least one of the $R_1$ and $R_2$ groups comprises at least one iodine atom, and which are of a suitable radiopaque character;

4. cyclophosphazenes of the formula:

$$[(P\!\!=\!\!N)_n]$$
$$\overset{\displaystyle R_1}{\underset{\displaystyle R_2}{|}}$$

wherein:

$R_1$ and $R_2$ are the same as above, and the compound is subject to the same proviso and radiopacity criterion as stated above, and n is from 3 to 8.

Preferably, in the boron compounds (3.) and (4.) above, at least one of the $R_1$ and $R_2$ groups comprises functionality (e.g., —NH(CH$_3$) groups) imparting water solubility to the polyphosphazene or cyclophosphazene, as the case may be.

It will be understood in the foregoing that the $R_1$ and $R_2$ groups in successive —P=N— repeating units/moieties of the phosphazene compounds may be the same as, or different from, one another. For example, the $R_1$ groups in a first repeating unit or moiety of the phosphazene compound may be the same as or different from the $R_1$ group in the next and other repeating units/moieties in the phosphazene compound.

Preferred boron compounds which may be employed in the practice of the present invention include cyclophosphazenes of the formula:

$$[(N\!\!=\!\!P)_3]$$
$$\overset{\displaystyle R_1}{\underset{\displaystyle R_2}{|}}$$

wherein:

$R_1$ and $R_2$ are as defined above, and the compound is subject to the same proviso that at least one of the $R_1$ and $R_2$ substituents contains at least one boron atom, it being understood that the $R_1$ and $R_2$ groups joined to each of the phosphorous atoms in the compound may differ independently from one another, or, alternatively, all of the individual $R_1$ and $R_2$ groups, each of which is independently selected relative to the other, may be the same on the respective phosphorous atoms.

The various compounds described hereinabove may be administered for X-ray imaging applications in non-salt forms, as well as in the form of physiologically acceptable salts. Particularly preferred physiologically acceptable salts include, but are not limited to, sodium, potassium, calcium, and ammonium salts.

The contrast media reagents of the present invention may be employed in any suitable formulation. A useful contrast medium formulation typically comprises the active ingredient (i.e., the radiopaque boron compound) together with one or more physiologically acceptable carriers thereof and optionally any other therapeutic or desired ingredients. The carrier(s) must be physiologically acceptable in the sense of being compatible with the other ingredients of the formulation and not unsuitably deleterious to the recipient thereof. The active reagent ingredient is provided in an amount effective to achieve the desired radiopacity and radiological imaging effect, and in a quantity appropriate to such purpose.

By way of example, a radiological imaging contrast medium formulation of the present invention may comprise a sterile aqueous solution, for intravascular administration, as the diagnostic radiopaque medium employed in excretory urography, angiocardiography, or aortography, or in other contrast medium application. Such contrast medium formulation may usefully include salts and buffers rendering the sterile aqueous solution isotonic with the receiving locus of the corporeal system to which the contrast medium formulation is administered. Useful salt/buffer ingredients may include calcium disodium, and monobasic sodium phosphate buffer. Desirably, at least 15% by weight, based on the total weight of solution, of the formulation is chemically bound iodine deriving from boron compounds of the present invention, preferably at least 40%, and most preferably at least 50%, of iodine, on such weight basis.

In addition to the boron compound(s), the contrast medium reagent formulation of the present invention may include salts and buffers, as mentioned, as well as diluents, binders, disintegrants, surface active agents, thickeners, preservatives (including anti-oxidants), and the like.

The administration of the boron compound-containing contrast medium formulation to the corporeal situs to be visualized, may be carried out in any suitable manner and with any efficacious means and methods. For example, the intravascular administration of contrast medium formulation may be effected by a catheter joined at one end to a vascular locus and in fluid introduction relationship therewith. The other end of the catheter may be joined to a suitable angiographic syringe, such as a Coeur 150 ml angiographic syringe, commercially available from Coeur Laboratories, Inc. (Raleigh, N.C.), as employed in a Medrad Mark V ® angiographic injector, commercially available from Medrad, Inc. (Pittsburgh, Pa.).

The dosage of the contrast medium formulation, in the administration of the formulation to the corporeal situs, may be at any suitable level consistent with the imaging function to be carried out. By way of example, a formulation containing approximately 40% chemically bound iodine deriving from boron compound(s) therein, may be usefully employed for urographic, angiocardiographic, and/or aortographic applications, at an intravenous dosage in adults of 25-50 ml of the formulation, injected over a period of 15-120 seconds, and more preferably over a period of 30-90 seconds, so that peak blood values are obtained immediately following injection, and equilibration with extracellular compartments is attained in approximately 5-15 minutes.

It will be recognized that the foregoing composition, dosage, and administration parameters are illustrative in character, and that the composition, dosage, and administration techniques may be varied widely within the broad practice of the present invention, within the skill of the relevant art.

Set out below is a description of the synthesis of borohydride compounds and salts, including halogenated derivatives comprising iodine reagent compounds potentially useful in the broad practice of the present invention.

It has been known since the early 1960's that salts of $B_{12}H_{12}^{2-}$ are thermally stable, and resistant toward degradation by acids, bases, and mild oxidizing agents, to a degree which is unique in boron hydride chemistry. The $B_{12}H_{12}^{2-}$ anion does react, however, with a variety of reagents to produce substitution derivatives, including halogen derivatives, which rival or exceed the thermal and chemical stability of $B_{12}H_{12}^{2-}$, and are potentially usefully employed in the practice of the present invention.

The icosahedral $B_{12}$ framework provides the basis for an entirely new generation of contrast media (CM) agents. The properties of the parent moiety, $B_{12}H_{12}^{2-}$, will be briefly described below, followed by a description of various halogenated (iodinated) species based on same.

Salts of $B_{12}H_{12}^{2-}$.

a. Thermal Stability

By way of illustration, $Cs_2B_{12}H_{12}$ can be heated to 810° C. in an evacuated sealed quartz tube and recovered unchanged. It is also quite thermally stable in air.

b. Hydrolytic Stability $B_{12}H_{12}^{2-}$ salts show no reaction with strong aqueous sodium hydroxide even at 95° C. $B_{12}H_{12}$ c. Solubility Extremely water soluble salts of $B_{12}H_{12}^{2-}$ are formed with cations such as ammonium, lithium, sodium and alkaline earths.

d. Toxicity

The approximate lethal dose of $Na_2B_{12}H_{12}$, administered orally to rats, is greater than 7.5 gm/kg of body weight. This is approximately equal to the oral toxicity of sodium chloride. Massive doses of a closely related derivative, $Na_2B_{10}H_{10}$, have been given to humans without serious effect and the anion recovered from urine specimens. Such biological inertness is attributed to its chemical stability.

e. Structure

The twelve boron atoms in the $B_2H_{12}^{2-}$ anion have icosahedral symmetry, and each boron atom has an exopolyhedral hydrogen bond.

The volume of the $B_{12}H_{12}^{2-}$ ion is comparable to that swept out by a rotating benzene group.

f. Cost $B_{12}H_{12}^{2-}$ salts can be made in very large quantities and at reasonable cost.

Halogenated Derivatives of $B_{12}H_{12}^{2-}$

Partially or completely chlorinated, brominated, and iodinated derivatives of $B_{12}H_{12}^{2-}$ have been prepared (see Knoth, W.H., et al, Inorg. Chem., 3, 159 (1964)).

Salts of $B_{12}I_{12}^{2-}$ a. Thermal Stability

The $B_{12}I_{12}^{2-}$ dianion, which contains about 93% iodine, suffers no degradation in 20% aqueous NaOH at 85° C., or $H_2SO_4$ at 150° C. Thus, its salts can be very easily sterilized. This remarkable stability suggests that this anion probably has very little toxicity, and also implies that there is essentially no dissociation to give free I-.

c. Solubility $Na_2B_{12}I_{12}$ is freely soluble in water.

d. Preparation

For the preparation of iodinated salts of $B_{12}H_{12}^{2-}$ (Knoth W.H., et al, ibid), the first two iodine atoms can be placed on the icosahedral cage by reaction of $I_2$ in accordance with the equation:

$$Na_2B_{12}H_{12} + 2I_2 \rightarrow Na_2B_{12}H_{10}I_2 + 2HI.$$

The reaction is complete in 10 minutes at room temperature. Solvents such as 1,1,2,2-tetrachloroethane or CClZ$_4$ can be used. Even at this stage, the percent iodine in B$_{12}$H$_{10}$I$_2{}^{2-}$ is high (57.7%).

The remaining iodine atoms are added by reaction of Na$_2$B$_{12}$H$_{10}$I$_2$ with ICl:

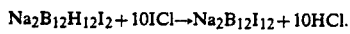

Table I below presents molecular weight data on some B$_{12}$H$_{12}{}^{2-}$ salts and iodinated derivatives and the % iodine in the latter.

TABLE I

Molecular Weight of B$_{12}$H$_{12}{}^{2-}$ Salts, Iodinated B$_{12}$ Salts and % Iodine

| Hydride Salts | M. Wt. | Iodinated Salts | M. Wt. | % I |
| --- | --- | --- | --- | --- |
| Li$_2$B$_{12}$H$_{12}$ | 155.6 | Li$_2$B$_{12}$I$_{12}$ | 1654 | 92.1 |
| Na$_2$B$_{12}$H$_{12}$ | 187.7 | Na$_2$B$_{12}$I$_{12}$ | 1700 | 89.6 |
| | | MgB$_{12}$I$_{12}$ | 1678 | 90.8 |
| Cs$_2$B$_{12}$H$_{12}$ | 407.5 | Cs$_2$B$_{12}$I$_{12}$ | 1919 | 79.4 |
| | | Na$_2$B$_{12}$F$_4$I$_8$ | 1268 | 80.1 |
| | | Na$_2$B$_{12}$H$_4$I$_8$ | 1196 | 84.5 |
| | | Na$_2$B$_{12}$H$_{10}$I$_2$ | 440 | 57.7 | e. Toxicity

The extreme inertness of B$_{12}$I$_{12}{}^{2-}$ suggests that its toxicity characteristics are similar to those of B$_{12}$H$_{12}{}^{2-}$. Based on toxicity characteristics of Na$_2$B$_{12}$I$_{12}$ which are equivalent to those observed for Na$_2$B$_{12}$H$_{12}$ containing approximately 63 gm I/kg body weight may be usefully employed for radiological imaging applications.

f. Osmality Considerations

X-ray contrast agents based upon polyiodinated benzene derivatives are customarily formulated such that 100 cm$^3$ of sterile solution containing 32 grams of iodine (60 grams of whole product) are injected. This represents a water solubility of about 1M.

For Na$_2$B$_{12}$I$_{12}$ (89.6% I) to obtain 32 gm I in 100 cm$^3$ of solution, only 35.7 gm of Na$_2$B$_{12}$I$_{12}$ are needed. The resulting solution is 0.21 M in Na$_2$B$_{12}$I$_{12}$.

Since osmality is proportional to the number of dissolved particles, a 0.21 M solution of Na$_2$B$_{12}$I$_{12}$ would (ideally) behave as a 0.63 M solution of a non-ionic contrast agent. Thus, even though Na$_2$B$_{12}$I$_{12}$ is an ionic compound, because of its exceptionally high iodine percent, the osmality of solutions containing the required amount of iodine (32 gm I/100 cm$^5$) would (ideally) still be less than non-ionic organic iodinated solutions of approximate 1M.

Solutions of B$_{12}$I$_{12}{}^{2-}$ of lower osmality than those of the sodium salts can be made, e.g., utilizing MgB$_{12}$I$_{12}$. Passage of Na$_2$B$_{12}$I$_{12}$ through an acid ion exchange column may be employed to produce the conjugate acid, (H$_3$O+)$_2$B$_{12}$I$_{12}$·xH$_2$O, followed by reaction with MgO or MgCO$_3$ to give MgB$_{12}$I$_{12}$:

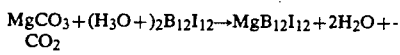

A 0.21M solution of MgB$_{12}$I$_{12}$ (90.8% I) contains 32 gm, I/100 cm$^3$, and behaves (osmality-wise) as a 0.42 M solution of a non-ionic compound.

By way of comparison, a 0.42M solution of Iotrol (molecular weight 1,626 and 46.8% I), 32 gm I/100 cm$^3$, has an osmality of 300; thus, a 0.21M solution of MgB$_{12}$I$_{12}$ (0.42M in particles) has an ideal osmality comparable to Iotrol.

g Synthesis

Li$_2$B$_{12}$H$_{12}$ and Na$_2$B$_{12}$H$_{12}$ can be made in almost quantitative yield from LiBH$_4$ or NaBH$_4$. The theoretical yield of Na$_2$B$_{12}$I$_{12}$ from 1 kg of Na$_2$B$_{12}$H$_{12}$ is 1×1700/187.7=9.06 kg.

The laboratory preparation of Na$_2$B$_{12}$I$_{12}$ involves only the addition of I$_2$ followed by ICl (to a solution of Na$_2$B$_{12}$I$_{12}$), or essentially a one-step reaction.

h. Viscosity Considerations 32 grams of I per 100 cm$^3$ of solution is easily obtained by solutions of B$_{12}$I$_{12}{}^{2-}$ around 0.2M; viscosity is acceptably low.

i. Water Stability

Salts of B$_{12}$I$_{12}{}^{2-}$ are readily sterilizable. B$_{12}$I$_{12}{}^{2-}$ suffers no degradation in H$_2$SO$_4$ at 150° C., or in 20% aqueous NaOH at 85° C.

Derivative Formation

There is an extensive literature on the derivatization of B$_{12}$H$_{12}{}^{2-}$ (and B$_{10}$H$_{10}{}^{2-}$) which is concisely described in "The Chemistry of Boron and Its Compounds", Earl L. Muetterties, Ed., Chapter 6, Boron Hydrides, by M. F. Hawthorne, John Wiley & Sons, Inc., N.Y. (1967), the disclosure of which hereby is incorporated herein by reference.

One general approach to derivative synthesis is direct substitution on B$_{12}$H12$^{2-}$, followed by modification of the species thus formed (including halogenation). One attractive feature of the derivative chemistry of B$_{12}$H$_{12}{}^{2-}$ is that substitution can bring about a change in net charge, yielding the possibility of preparing (iodinated) polyhedral boron compounds of varying charge. Thus, anions, e.g., of net −1 charge, neutral species, and even cations are feasible.

A list of substituted B$_{12}$H$_{12}{}^{2-}$ species and their analogs (iodinated derivatives) is set out in Table II below.

TABLE II

Substituted B$_{12}$H$_{12}{}^{2-}$ Species and Related Iodinated (or Brominated) Derivatives

| Substituted B$_{12}$H$_{12}{}^{2-}$ | Iodinated (or Brominated) Derivatives |
| --- | --- |
| B$_{12}$H$_{11}$OH$^{2-}$ | B$_{12}$I$_{11}$(OH)$^{2-}$ |
| B$_{12}$H$_{10}$(OH)$_2{}^{2-}$ | B$_{12}$I$_{10}$(OH)$_2{}^{2-}$ |
| B$_{12}$H$_{10}$(COOH)$_2{}^{2-}$ | B$_{12}$I$_{10}$(COOH)$_2{}^{2-}$ |
| B$_{12}$H$_{10}$(CO)$_2$ | B$_{12}$I$_{10}$(CO)$_2$ |
| B$_{10}$H$_8$(CO)$_2$ | B$_{10}$I$_8$(CO)$_2$ |
| B$_{12}$H$_{10}$(N$_2$)$_2$ | B$_{12}$I$_{10}$(N$_2$)$_2$ |
| B$_{12}$H$_{10}$[N(CH$_3$)$_2$CH$_2$Cl]$^{2-}$ | B$_{12}$I$_{10}$[N(CH$_3$)$_2$CH$_2$Cl]$^{2-}$ |
| B$_{12}$H$_{10}$(NH$_3$)$_2$ | B$_{12}$I$_{10}$(NH$_3$)$_2$ |

The examples shown in Table II above are illustrative of a wide variety of potential halogen-substituted polyhedral boron species. Most have outstanding hydrolytic and oxidative stability, and high halogen content.

A particularly advantageous contrast media reagent formulation comprises B$_{12}$I$_{10}$(NH$_3$)$_2$. This non-ionic derivative contains close to 89% I and is water-soluble. There are a number of routes to its preparation. Other particularly preferred reagent species include B$_{12}$I$_{10}$(CH$_2$NH$_3$)$_2$ and B$_{12}$I$_{10}$(CH$_2$OH)$_2{}^{2-}$.

Molecular dimers of the halogenated polyhedral boron compounds may be synthesized to produce radiopaque particles which are larger than normal capillaries fenestration. This limits distribution of the boron compounds to the intravascular space in the use of contrast media formulations containing such boron compounds.

Cyclophosphazene- and Polyphosphazene-Based Contrast Media Agents

Cyclophosphazenes and polyphosphazenes constitute a class of compounds which may be employed as "backbone" or "framework" chemical structures to which active moieties of currently used contrast media agents, as well as active moieties of the above-discussed boron species, may be attached.

Cyclophosphazenes, such as $(Cl_2PN)_3$, are based on alternating P and N atoms:

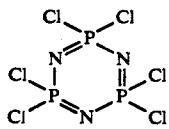

More specifically, cyclophosphazenes usefully employed in the broad practices of the present invention have the following formula:

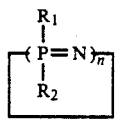

wherein:

$R_1$ and $R_2$ may be the same or different, and are independently selected from hydrogen, halo, and organo groups (e.g., alkyl, haloalkyl, aryl, arylalkyl, alkenyl, alkylamino, arylamino, etc.); and n is from 3 to 8;

with the proviso that at least one of the $R_1$ and $R_2$ groups comprises at least one iodine atom, and that the compound is of a radiopaque character.

Polyphosphazenes comprise a P-N chain backbone and have the following formula:

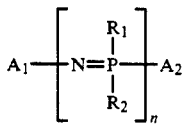

wherein:

$A_1$, and $A_2$ are end groups which may be of any suitable organic constituency which is compatible with the polyphsophazene and does not preclude its efficacy for radiological imaging purposes-$A_1$ and $A_2$ may be the same or different, and may for example comprise alkyl or other hydrocarbyl radicals;

$R_1$ and $R_2$ may be the same or different, and are independently selected from hydrogen, halo, and organo groups (e.g., alkyl, haloalkyl, aryl, arylalkyl, alkenyl, alkylamino, arylamino, etc.); and n is from 2 to 20,000;

with the proviso that at least one of the $R_1$ and $R_2$ groups comprises at least one iodine atom; and which is of a suitable radiopaque character.

The compound $(Cl_2PN)_3$ is a white, crystalline material prepared from phosphorous pentachloride and ammonium chloride. The P-Cl bonds are highly reactive, reacting readily with nucleophiles such as alkoxides, aryloxides, amines, etc., to give completely substituted derivatives.

The $(Cl_2PN)_3$ compound may be usefully employed to construct "non-ionic" contrast media agents. For example, a triodo benzene species could be used to partially derivativatize the $(Cl_2PN)_3$ ring, followed by derivatization with appropriate groups to confer aqueous solubility:

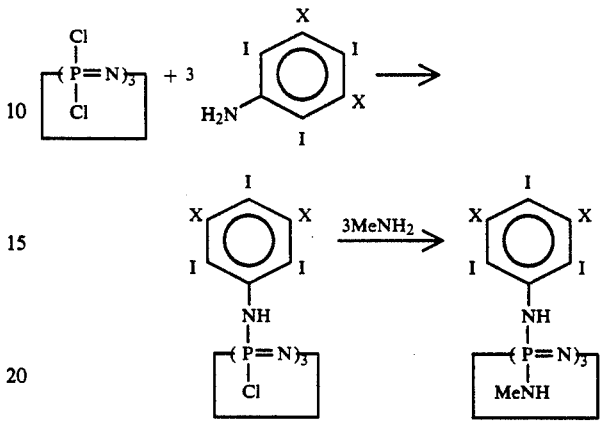

wherein X=H and $H_2O$ solubility is conferred by the MeNH groups on the phosphorous atoms of the compound.

Instead of the above-described halogenated benzenes, halogenated boron compounds may be usefully employed to synthesize boron-based contrast media reagents according to the present invention. Thus, species such as shown below can be constructed which are non-ionic, and possess high water solubility and high I content:

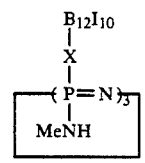

wherein X is an appropriate linking or bridge moiety, e.g., an amino or alkoxide linker moiety.

Synthesis of polyphosphazenes may be effected as shown below:

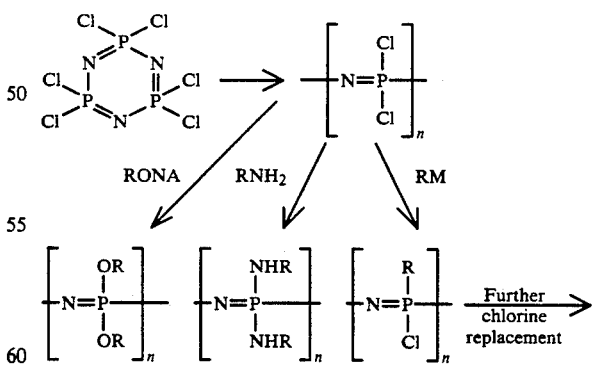

The reactive chloride atoms of the starting material in these reactions can be replaced with nucleophiles such as amines, alkoxides, aryloxides, etc.

Of particular interest in the manufacture of contrast media reagents according to the present invention is the synthesis approach of partial substitution of $Cl^-$ with triiodinated phenoxide or iodinated $B_{12}$ species. The remaining chlorides then can be replaced with substituents to confer water solubility, such as MeNH-, glycerol, etc.

The water-soluble polyphosphazene polymers described above desirably contain hydrolyzable groups capable of producing a degradable polymer. For example, an amino acid such as glycine can be attached via a P-N bond. Hydrolysis of the P-N bonded amino acids gives a P-OH bond. The hydrophosphazenes are hydrolytically unstable, decomposing to harmless phosphate and ammonia, thereby permitting a highly iodinated polymeric contrast media reagent to be synthesized with the capability to eventually erode and be excreted from the body.

The features and advantages of the present invention are more fully shown by the following non-limiting examples, wherein all parts and percentages are by weight, unless otherwise expressly stated.

EXAMPLE I 35.7 grams of $Na_2B_{12}I_{12}$ are added to a sterile aqueous solution buffered with a monobasic sodium phosphate buffer, to provide 100 cc of solution. 50 milliliters of the resulting solution are intravenously administered over a period of approximately 60 seconds, using a Coeur ® 150 ml angiographic syringe (Coeur Laboratories, Inc., Raleigh, N.C.) connected by a luer-lock coupling to a catheter which is joined at its opposite end by venous shunt to the vascular administration site. The administration is effected by a Mark V ® angiographic power injector (Medrad Corporation, Pittsburgh, Pa.), with the syringe being appropriately positioned in the injector jacket of the automatic injector apparatus. Peak blood values are attained immediately following injection. The blood concentration falls rapidly over the next 5-10 minutes, and equilibration with the extracellular compartments is attained in approximately 10 minutes. The vascular situs is visualized by impingement of an X-ray beam on such situs, from an X-ray generator comprising an X-ray tube with a collimator serving as a beam-limiting device. The X-ray beam has a photon energy of above 20 keV.

A radiographic image is produced of the vascular situs, and is employed to determine whether occlusion of the vascular lumen has occurred and whether angioplasty is an appropriate therapeutic intervention.

The contrast media formulation is excreted rapidly unchanged by renal glomerular filtration.

EXAMPLE II

The procedure of Example I is repeated using a contrast media formulation comprising $B_{12}I_{10}(NH_3)_2$, and the efficacy of such reagent compound is demonstrated.

EXAMPLE III

The procedure of Example I is repeated with various cyclophosphazenes and polyphosphazenes, comprising at least 40% iodine deriving from boroiodide pendent functionality which is bonded directly or indirectly (via an amino or alkoxide divalent linker group) to a phosphorous atom of the reagent, and the efficacy of such reagent compounds is demonstrated.

While the invention has been described hereinabove with respect to various specific embodiments, formulations, and aspects, it will be appreciated that numerous variations, modifications, and other embodiments may be employed, and accordingly, all such variations, modifications, and embodiments are to be regarded as being within the spirit and scope of the invention.

What is claimed is:

1. A cyclophosphazene of the formula:

wherein:

$R_1$ and $R_2$ may be the same or different, and are independently selected from hydrogen, halo, alkyl, alkoxy, haloalkyl, aryl, aryloxy, arylalkyl, alkenyl, amino, alkylamino, and arylamino groups; and n is from 3 to 8;

with the proviso that at least one of the $R_1$ and $R_2$ groups comprises boroiodide functionality.

2. A cyclophosphazene according to claim 1, wherein n is 3.

3. A cyclophosphazene according to claim 1, wherein at least one of the $R_1$ and $R_2$ groups comprises at least one water solubility-imparting functionality.

4. A cyclophosphazene according to claim 3, wherein said at least one water solubility-imparting functionality is selected from the group consisting of MeNH-groups, glycerol groups, amino acid groups, and —OH groups.

5. A cyclophosphazene of the formula:

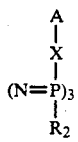

wherein:

A is borohydride functionality of triiodophenyl;

X is a divalent amino or alkoxide linker moiety; and $R_2$ is a water solubility-imparting functional group.

6. A cyclophosphazene of the formula:

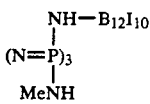

7. A cyclophosphazene of the formula:

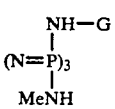

wherein G is triiodophenyl.

* * * * *